(12) United States Patent
Liu et al.

(10) Patent No.: US 12,060,389 B1
(45) Date of Patent: Aug. 13, 2024

(54) ENTEROVIRUS MULTI-ANTIGEN EPITOPE FUSION PROTEIN, GENE, VACCINE, AND PREPARATION METHOD THEREOF

(71) Applicant: Institute of Medical Biology, Chinese Academy of Medical Sciences, Kunming (CN)

(72) Inventors: Longding Liu, Kunming (CN); Huiwen Zheng, Kunming (CN); Heng Li, Kunming (CN); Xin Zhao, Kunming (CN); Li Yu, Kunming (CN); Guorun Jiang, Kunming (CN); Dandan Li, Kunming (CN); Heng Zhao, Kunming (CN); Ying Zhang, Kunming (CN); Yun Liao, Kunming (CN); Haijing Shi, Kunming (CN)

(73) Assignee: INSTITUTE OF MEDICAL BIOLOGY, CHINESE ACADEMY OF MEDICAL SCIENCES, Kunming (CN)

( * ) Notice: Subject to any disclaimer, the term of this patent is extended or adjusted under 35 U.S.C. 154(b) by 0 days.

(21) Appl. No.: 18/412,485

(22) Filed: Jan. 13, 2024

(30) Foreign Application Priority Data

Oct. 23, 2023 (CN) .......................... 202311370867.1

(51) Int. Cl.
| | | |
|---|---|---|
| *C07K 14/005* | (2006.01) | |
| *C07K 14/435* | (2006.01) | |
| *C12N 15/85* | (2006.01) | |
| *A61K 39/00* | (2006.01) | |

(52) U.S. Cl.
CPC .......... *C07K 14/005* (2013.01); *C07K 14/435* (2013.01); *C12N 15/85* (2013.01); *A61K 39/00* (2013.01); *A61K 2039/55505* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 10,744,199 B2 * | 8/2020 | Kanekiyo | .............. | C07K 14/00 |
| 11,149,254 B2 * | 10/2021 | Szalay | .................... | A61P 35/04 |

OTHER PUBLICATIONS

Institute of Medical Biology, Chinese Academy of Medical Sciences (Applicant), Supplemental amendment for CN202311370867.1, w/ replacement claims (allowed), Nov. 3, 2023.
CNIPA, Notification to grant patent right for invention in CN202311370867.1, Nov. 29, 2023.

\* cited by examiner

*Primary Examiner* — Agnieszka Boesen
(74) *Attorney, Agent, or Firm* — Zhigang Ma

(57) ABSTRACT

An enterovirus multi-antigen epitope fusion protein, a gene, a vaccine and a preparation method thereof are provided, relating to the field of vaccine preparation technologies. The amino acid sequence of the enterovirus multi-antigen epitope fusion protein is shown in SEQ ID NO: 4. The vaccine is prepared by adopting the preparation method of a genetically engineered protein vaccine, and the prepared vaccine has stronger specificity. After protein purification, there are fewer impure proteins and more specific antigen proteins, thus improving the effectiveness and safety of the combined vaccine.

8 Claims, 4 Drawing Sheets

Specification includes a Sequence Listing.

ENTEROVIRUS MULTI-ANTIGEN EPITOPE FUSION PROTEIN, GENE, VACCINE, AND PREPARATION METHOD THEREOF

TECHNICAL FIELD

The disclosure relates to the field of vaccine preparation technologies, and more particularly to an enterovirus multi-antigen epitope fusion protein, a gene, a vaccine and a preparation method thereof.

STATEMENT REGARDING SEQUENCE LISTING

The sequence listing associated with this application is provided in text format in lieu of a paper copy and is hereby incorporated by reference into the specification. The name of the XML file containing the sequence listing is 23138TBYX-USP1-SL.xml. The XML file is 12,047 bytes; is created on Dec. 25, 2023; and is being submitted electronically via Patent Center.

BACKGROUND

Hand-foot-mouth disease (HFMD, also referred to as hand, foot, and mouth disease) is an infectious disease caused by enteroviruses, which is commonly found in children under 5 years of age. Children with HFMD show mild clinical symptoms, such as runny nose, cough, fever, rash on hands, feet and mouth, and in severe cases symptoms of central nervous system paralysis, mainly including encephalitis, meningitis, encephalomyelitis, neuroinflammatory pulmonary edema, and so on. The main pathogens of HFMD are now known to be the genus enterovirus A, among which the main pathogens causing HFMD include enterovirus A71 (EV-A71), coxsackievirus A16 (CV-A16), CV-A10 and CV-A6. At present, there is no specific drug for treating HFMD, and there is an inactivated EV-A71 vaccine on the market. However, it was found that the inactivated EV-A71 vaccine could not effectively prevent the infection of other pathogens causing HFMD, including viruses such as CV-A10, CV-A6, and CV-A16. Therefore, the development of a combined vaccine of EV71-CA16-CA10-CA6 plays an important role in effectively inhibiting EV-A71, CV-A16, CV-A10 and CV-A6 pathogens simultaneously.

In recent years, the design of nanoparticle vaccine by epitope tandem has been widely used in influenza virus vaccine and has good immunogenicity. This vaccine design method based on antigen-antibody interaction has also been applied to many pathogens including respiratory syncytial virus (RSV) and Ebola virus. According to the structural analysis of enteroviruses, the BC, DE, GH and EF loop regions of the main structural proteins VP1, VP2 and VP3 of enterovirus have been confirmed to contain neutralizing sites of the enteroviruses. Therefore, connecting these domains including key neutralizing epitopes together for reverse vaccinology design will provide ideas for the development of new combined vaccines for enteroviruses.

Vaccines with tandem epitopes usually have weak immunogenicity. Therefore, in the research, nanoparticle vectors are usually used to connect gene fragments of the target protein to prepare protein vaccines, so as to increase the number and frequency of immunogen expression and improve the immunogenicity of antigen fragments. In recent years, Ferritin nanoparticle vector has been widely used in the preparation of a genetically engineered protein vaccine. The Ferritin protein monomer expressed by an expression vector constructed on the basis of the nanoparticle vector can self-assemble into a spherical structure in cells, and the target protein can be fused and displayed on the surface of the sphere. The nanoparticle vaccine can effectively present the protein antigen and induce a strong immune response. Among the above technologies, the nanoparticle vaccine technology using Ferritin as a vector has successfully developed subunit vaccines including coronavirus (COVID-19) vaccines and influenza vaccines. Therefore, enterovirus epitope vaccines adopting Ferritin nanoparticles to demonstrate antigen epitopes in different key protein regions will effectively increase the frequency and density of epitope demonstration to provide vaccine immunogenicity.

SUMMARY

The preparation of a Ferritin nanoparticle vaccine with enterovirus 71 (EV71), coxsackievirus A16 (CA16), CA10, and CA6 key antigen epitopes in tandem is innovative and necessary for the development of an enterovirus combined vaccine. The disclosure provides a design and a preparation method of an EV71-CA16-CA10-CA6 tandem multi-epitope vaccine for hand, foot, and mouth disease (HFMD), which can effectively resist the infection of these four kinds of enteroviruses to prevent the occurrence of HFMD.

In order to achieve the above objective, the disclosure provides the following technical solutions.

The disclosure provides an enterovirus multi-antigen epitope fusion protein, and the amino acid sequence of the enterovirus multi-antigen epitope fusion protein is shown as SEQ ID NO: 4.

In an embodiment, the enterovirus multi-antigen epitope fusion protein includes antigen epitopes of VP1, VP2 and VP3 of the EV71; antigen epitopes of VP1, VP2 and VP3 of the CA16; antigen epitopes of VP1, VP2 and VP3 of the CA10, and antigen epitopes of VP1, VP2 and VP3 of the CA6.

In an embodiment, the enterovirus multi-antigen epitope fusion protein is composed of an EF loop region and a GH loop region of an EV71 VP1 protein, an EF loop region of an EV71 VP2 protein, and a GH loop region of EV71 VP3 protein; an EF loop region and a GH loop region of a CA16 VP1 protein, an EF loop region of a CA16 VP2 protein, and a GH loop region of a CA16 VP3 protein; a BC loop region, a DE loop region, an EF loop region, a GH loop region, and an HI loop region of a CA6 VP1 protein, an EF loop region of a CA6 VP2 protein, and a GH loop region of a CA6 VP3 protein; an EF loop region and a GH loop region of a CA10 VP1 protein, an EF loop region of a CA10 VP2 protein, and a GH loop region of a CA10 VP3 protein, which are sequential tandem.

In an embodiment, the regions of the enterovirus multi-antigen epitope fusion protein are connected by spacer sequences (also referred to as intervening sequences). The spacer sequence is GGSSGG shown as SEQ ID NO: 6, SGG, or EAAAK shown as SEQ ID NO: 7.

The disclosure provides a gene encoding the enterovirus multi-antigen epitope fusion protein.

The disclosure provides an expression cassette, a recombinant vector, or a cell containing the gene.

In an embodiment, the cell is a 293T cell or a Chinese hamster ovary (CHO) cell.

In an embodiment, the recombinant vector includes but is not limited to pcDNA™3.1⁺, etc.

In an embodiment, the expression cassette is connected to a regulatory sequence for regulating an expression of a target nucleic acid gene sequence, including but not limited to a promoter, an enhancer, a signal peptide coding sequence, a terminator, a histidine (HIS) tag, etc.

The disclosure provides an enterovirus multi-antigen epitope combined vaccine, which includes the enterovirus multi-antigen epitope fusion protein, a Ferritin protein (the nucleotide sequence of the Ferritin protein is the $1^{st}$ to $501^{st}$ bases in the sequence of SEQ ID NO: 1), and an adjuvant.

In an embodiment, the adjuvant is one selected from the group consisting of an aluminum hydroxide adjuvant, an aluminum phosphate adjuvant, and an aluminum sulfate adjuvant.

In an embodiment, a final concentration of aluminum content of the adjuvant is in a range of 0.1-0.4 micrograms per milliliter (mg/mL) in terms of aluminum ion $Al3^+$ content.

The disclosure also provides a preparation method of a nanoparticle tetravalent enterovirus multi-epitope vaccine with a Ferritin protein as a carrier, which specifically includes the following steps: fusing the enterovirus multi-antigen epitope fusion protein with the Ferritin protein to obtain a Ferritin-EV71-CA16-CA6-CA10; transforming the Ferritin-EV71-CA16-CA6-CA10 into a nucleotide sequence, constructing an expression vector of pcDNA™3.1$^+$-Ferritin-EV71-CA16-CA6-CA10, and obtaining the multi-epitope vaccine protein after expression, separation and purification; and after adsorption of an adjuvant, the tandem epitope vaccine is obtained.

In an embodiment, the above expression plasmid is transfected into mammalian cells for expression by cationic liposomes, such as Lipofectamine™ 2000 (LF2000), polyethylenimine (PEI), or FuGENE®. Then the recombinant protein expressed above is extracted and purified. The purpose of protein purification is to obtain the expected size of the target protein.

In an embodiment, the purification methods include but are not limited to affinity chromatography, ion exchange, etc.

Enterovirus particles are single-stranded positive-strand ribonucleic acid (RNA) viruses with a size of about 30 nanometers (nm). When the virus infects human cells and enters the cytoplasm, it will use its own viral RNA to be transcribed into a large monomeric polyprotein precursor, and the polyprotein precursor protein will be digested into a variety of mature proteins through the non-structural proteins $2A^{pro}$, $3C^{pro}$, and $3CD^{pro}$ of the virus, including capsid proteins VP0, VP1, VP3, and proteins 2A, 2B, 2C and 3A, 3B, 3C, 3D related to viral replication. Subsequently, the RNA induces the processing of VP0 into VP2 and VP4 to produce mature virus particles (Jim Baggen et al., "The life cycle of non-polio enteroviruses and how to target it", Nature Reviews Microbiology, 2018, pp. 368-381, Vol. 16). The surface of enterovirus particles is mainly composed of subunits VP1, VP2 and VP3, which all adopt the typical eight-stranded antiparallel β-barrel folded state in their subunit structure, making each enterovirus have unique antigenicity (Infectious Diseases of the Fetus and Newborn (Seventh Edition, 2011)). There are several highly variable loops on the surface of viral capsid protein, and the loops are easily accessed by the host immune system, which is also the reason for the high antigenic diversity of enteroviruses. Therefore, the structural proteins VP1, VP2, and VP3 of EV71, CA16, CA10, and CA6 viruses contain antigen epitope regions that induce the production of enterovirus-neutralizing antibodies, and cell receptor binding sites (also referred to as cell-recognition sites).

The disclosure is based on the protein structural characteristics of the above-mentioned virus itself and the structural characteristics of the region that induces the production of neutralizing antibodies in the body. In the disclosure, the EF loop region and the GH loop region of the CA16 VP1 protein, the EF loop region of the CA16 VP2 protein, and the GH loop region of the CA16 VP3 protein; the BC loop region, the DE loop region, the EF loop region, the GH loop region, and the HI loop region of the CA6 VP1 protein, the EF loop region of the CA6 VP2 protein, and the GH loop region of the CA6 VP3 protein; the EF loop region and the GH loop region of the CA10 VP1 protein, the EF loop region of the CA10 VP2 protein and the GH loop region of the CA10 VP3 protein; the EF loop region and the GH loop region of the EV71 VP1 protein, the EF loop region of the EV71 VP2 protein, and the GH loop region of the EV71 VP3 protein are selected. In the early stage of the disclosure, the enterovirus antigen epitopes are screened by enterovirus-specific monoclonal antibodies, and the antigen epitopes of EV71, CA16, CA10 and CA6, the connection sequence between the segments, and the spacer amino acid sequence are predicted and analyzed by combining with bioinformatics software, so as to design a tandem multi-epitope enterovirus protein vaccine containing four enterovirus key antigen epitope sequences.

Due to the small molecular weight of each loop region, the epitope vaccine mentioned above may lead to the problem of insufficient immunogenicity induced in vivo for each epitope region. In order to solve this problem, these epitopes are connected in tandem and fused with the Ferritin nanoparticle protein to form a nanoparticle multivalent enterovirus EV71-CA16-CA10-CA6 epitope vaccine.

In the disclosure, according to the amino acid sequences of the main structural proteins VP1, VP2 and VP3 of the virus strain, the amino acid composition of the designed tandem peptide segment is characterized in that: the disclosure follows the sequence of Ferritin, EV71 (VP1-GH loop), EV71 (VP1-GH loop), EV71 (VP2-EF loop), EV71 (VP3-GH loop), CA16 (VP1-EF loop), CA16 (VP1-GH loop), CA16 (VP2-EF loop), CA16 (VP3-GH loop), CA6 (VP1-BC loop), CA6 (VP1-DE loop), CA6 (VP1-EF loop), CA6 (VP1-GH loop), CA6 (VP1-HI loop), CA6 (VP2-EF loop), CA6 (VP3-GH loop), CA10 (VP1-EF loop), CA10 (VP1-GH loop), CA10 (VP2-EF loop), CA10 (VP3-GH loop), and EV71 (VP1-EF loop).

In the disclosure, the subunits of Ferritin and polypeptide epitopes are fused and expressed, so that the nanoparticle tetravalent enterovirus multi-epitope vaccine with Ferritin as the carrier can be obtained. The expression of the protein can be identified by Western Blot. After an animal is immunized by the enterovirus multi-epitope vaccine, the neutralization effect of the serum of the immunized animal on enteroviruses EV71, CA16, CA10 and CA6 is detected through micro-neutralization assay. The survival rate of suckling mice is observed by challenge experiment on suckling mice born by adult mice after immunization, so as to observe the protective effect of vaccine on suckling mice. The results show that the multivalent epitope vaccine of enterovirus EV71-CA16-CA10-CA6 could stimulate mice to produce a cellular immune response and specific serum-neutralizing antibodies against VP1, VP2, VP3 and other proteins, and has good immunogenicity and antigen specificity.

The disclosure has the following beneficial effects.

According to the disclosure, the EF loop and GH loop regions of the EV71 VP1 protein, the EF loop region of the EV71 VP2 protein and the GH loop region of the EV71 VP3 protein; the EF loop and GH loop regions of the CA16 VP1 protein, the EF loop region of the CA16 VP2 protein and the GH loop region of the CA16 VP3 protein; the BC loop, DE loop, EF loop, GH loop and HI loop regions of the CA6 VP1 protein, the EF loop region of the CA6 VP2 protein and the GH loop region of the CA6 VP3 protein; the EF loop and GH loop regions of the CA10 VP1 protein, the EF loop region of the CA10 VP2 protein and the GH loop region of the CA10 VP3 protein are screened. In this situation, a multi-epitope protein of enterovirus EV71-CA16-CA6-CA10 is designed in tandem with the above domains. After the protein is adsorbed with the aluminum adjuvant, the enterovirus multivalent epitope combined vaccine is prepared.

The combined vaccine of the disclosure is self-assembled into a polymer nanoparticle protein vaccine by connecting the key antigen epitopes of four main structural proteins of enterovirus pathogens in series and by fusion expression with Ferritin protein, so that the expression concentration of small fragments of polypeptide is effectively increased, and the defect of low immunogenicity of epitope vaccines is solved.

The combined vaccine of the disclosure contains the key antigen epitopes of the main structural proteins VP1, VP2 and VP3 of HFMD, and is proven to be effective in preventing HFMD caused by EV71, CA16, CA10 and CA6 viruses in the suckling mice. The research of the disclosure shows that all the antigens can induce a good immune effect after immunization, and have good immunogenicity and protection.

The multi-epitope combined vaccine provided by the disclosure can simultaneously prevent various enterovirus pathogens. The use of the combined vaccine can simplify the vaccination procedure. The vaccine adopts the preparation method of a genetically engineered protein vaccine, and the prepared vaccine has a stronger specificity. After protein purification, there are fewer impure proteins and more specific antigen proteins, which can improve the effectiveness and safety of the combined vaccine.

DETAILED DESCRIPTION OF EMBODIMENTS

Figure 1:
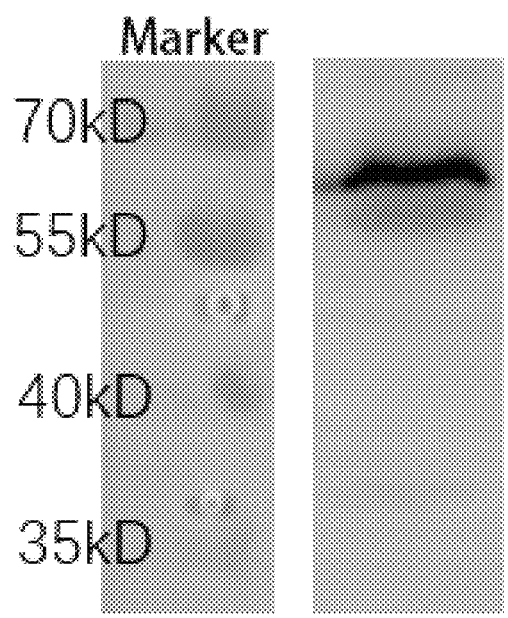
FIG. 1 illustrates a eukaryotic expression map of a multivalent vaccine recombinant protein detected by Western-Blot according to an embodiment 2 of the disclosure.

Technical solutions provided by the disclosure will be described in detail with embodiments below, but they cannot be understood as limiting the protection scope of the disclosure.

Embodiment 1

In this embodiment, an expression plasmid of an enterovirus EV71-CA16-CA6-CA10 quadruple multi-epitope vaccine of is constructed.

Specifically, an EF loop region and a GH loop region of an EV71 VP1 protein, an EF loop region of an EV71 VP2 protein, and a GH loop region of an EV71 VP3 protein; an EF loop region and a GH loop region of a CA16 VP1 protein, an EF loop region of a CA16 VP2 protein, and a GH loop region of a CA16 VP3 protein; a BC loop region, a DE loop region, an EF loop region, a GH loop region, and an HI loop region of a CA6 VP1 protein, an EF loop region of a CA6 VP2 protein, and a GH loop region of a CA6 VP3 protein; an EF loop region and a GH loop region of a CA10 VP1 protein, an EF loop region of a CA10 VP2 protein, and a GH loop region of a CA10 VP3 protein are sequentially connected in that order. The tandem antigen epitopes are connected between each antigen epitope by a spacer sequence GGSSGG shown as SEQ ID NO: 6 (the amino acid sequence of the tandem epitope protein containing the spacer sequence is shown in SEQ ID NO: 4, and the nucleotide sequence is shown in SEQ ID NO: 3).

Then, an expression plasmid vector of enterovirus Ferritin-EV71-CA16-CA6-CA10 quadruple multi-epitope vaccine is constructed, in which the nucleotide sequence of EV71-CA16-CA6-CA10 is located downstream of the nucleotide sequence of the Ferritin protein.

The amino acid sequence of Ferritin-EV71-CA16-CA6-CA10 of the multi-epitope vaccine designed in the early stage (as shown in SEQ ID NO: 2) is transformed into nucleotide sequence (as shown in SEQ ID NO: 1), and the base optimization is carried out. BGI Biotech Co., Ltd. is entrusted to carry out gene synthesis, and an expression vector of pcDNA™3.1$^+$-Ferritin-EV71-CA16-CA6-CA10 (the nucleotide sequence of the target gene is shown in SEQ ID NO: 5) is constructed. Sequencing proves that the insertion position of the target gene in the expression vector is correct without gene mutation.

Embodiment 2

In this embodiment, the eukaryotic expression of the recombinant protein pcDNA™3.1$^+$-Ferritin-EV71-CA16-CA6-CA10 is carried out.

The successfully constructed expression vector pcDNA™3.1$^+$-Ferritin-EV71-CA16-CA6-CA10 is transiently transfected into 293T cells. The specific method is as follows.

(1) Transfection experiment is carried out using a cell culture dish with a diameter of 15 centimeters (cm) and started when the cell fusion degree of 293T cells reached 80%.

(2) Before transfection, the complete medium containing 10% serum is replaced with serum-free medium.

(3) Lipofectamine™2000 reagent suspension is prepared, and the Lipofectamine™2000 reagent suspension is added to 1.5 milliliters (mL) of Opti-MEM™ medium.

(4) The expression plasmid of pcDNA™3.1$^+$-Ferritin-EV71-CA16-CA6-CA10 (the amount of expression plasmid to be added is calculated according to the mass-volume ratio of the plasmid to the Lipofectamine™2000 reagent suspension of 1 microgram abbreviated as μg:3 microliters abbreviated as μL) is added into 1.5 mL Opti-MEM™ medium.

(5) The solutions obtained by the steps (3) and (4) are mixed in equal volume, gently mixed, and then stood at 25° C. for 5 minutes to form a DNA-lipid complex.

(6) The DNA-lipid complex is mixed evenly (the total volume does not exceed 10% of the total culture medium volume) and then dropped into 293T cultured cells (without antibiotics).

(7) 5 hours after transfection, penicillin-streptomycin combined with antibiotics is supplemented and cultured in a 37° C. incubator for 72 hours.

(8) The expressed protein is obtained for Western-Blot (WB) detection. The WB detection results show that compared with the blank cells with only transfection reagent, the target protein band appeared at about 57.5 kilodaltons (kDa) in pcDNA™3.1⁺-Ferritin-EV71-CA16-CA6-CA10, which is consistent with the expected size of the recombinant protein size (FIG. 1).

Embodiment 3

In this embodiment, the recombinant protein in the above embodiment is purified.

Figure 2:
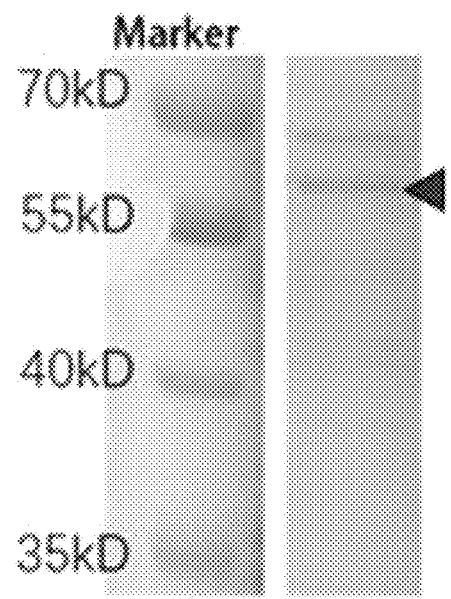
FIG. 2 illustrates a diagram showing purification of the recombinant protein analyzed by sodium dodecyl sulfate-polyacrylamide gel electrophoresis (SDS-PAGE) according to an embodiment 3 of the disclosure.

The expressed protein obtained in the embodiment 2 is purified by using a 5 mL gravity column, and the filled Ni Smart Beads 6FF gravity column is balanced at room temperature with 5 times the volume of sample buffer, and the balance is repeated 3 times. Subsequently, the sample is combined, and the sample is slowly added to the column-balanced gravity column to ensure that the sample and the medium are fully combined, and the effluent is collected and repeatedly loaded three times to increase the binding efficiency of the sample and the medium. Further, 15 times of column volume of washing buffer (20 millimoles per liter abbreviated as mM disodium hydrogen phosphate abbreviated as $NaH_2PO_4$, 500 mM NaCl, 5 mM imidazole, PH=8.0) is used for impure protein cleaning. The eluent (20 mM $NaH_2PO_4$, 500 mM NaCl, 250 mM imidazole, PH=8.0) is used to elute the target protein, and the effluent is collected. The sample of target protein effluent collected above is added into a dialysis bag, and dialyzed overnight with phosphate-buffered saline abbreviated as PBS (PH=7.4). Finally, sodium dodecyl sulfate-polyacrylamide gel electrophoresis (SDS-PAGE) staining is carried out, and the results show that a single band of high purity target protein is obtained, and the results of Western-Blot detection show that the target band with correct size is obtained (FIG. 2). In summary, after purification by Ni-ion affinity chromatography, a highly purified enterovirus multi-epitope recombinant protein vaccine can be obtained.

Embodiment 4

Preparation of Aluminum-Adsorbed Multiplex Recombinant Protein Vaccine.

Preparation of monovalent aluminum adsorption vaccine: aluminum adjuvant is diluted with 2 mM PBS at 3 mg/mL (calculated as $Al(OH)_3$), and the recombinant expression protein of pcDNA™3.1⁺-Ferritin-EV71-CA16-CA6-CA10 obtained in the embodiment 3 is diluted to 1 mg/mL with 2 mM PBS. The diluted aluminum adjuvant and the diluted recombinant protein are mixed in the same volume at room temperature, stirred by a magnetic stirrer and adsorbed for 1 hour at 25° C. to prepare the aluminum-adsorbed combined vaccine for HFMD. The detection and analysis of bicinchoninic acid (BCA) protein assay show that the adsorption efficiency of antigen protein reached over 90%. Subsequently, the recombinant protein vaccine adsorbed by the above aluminum hydroxide adjuvant is diluted into high, medium and low dose groups, with the recombinant protein concentrations of 50 micrograms per milliliter (μg/mL), 100 μg/mL, and 200 μg/mL respectively.

Embodiment 5

Immunogenicity Determination of Multi-Epitope Combined Vaccine

Figure 3:
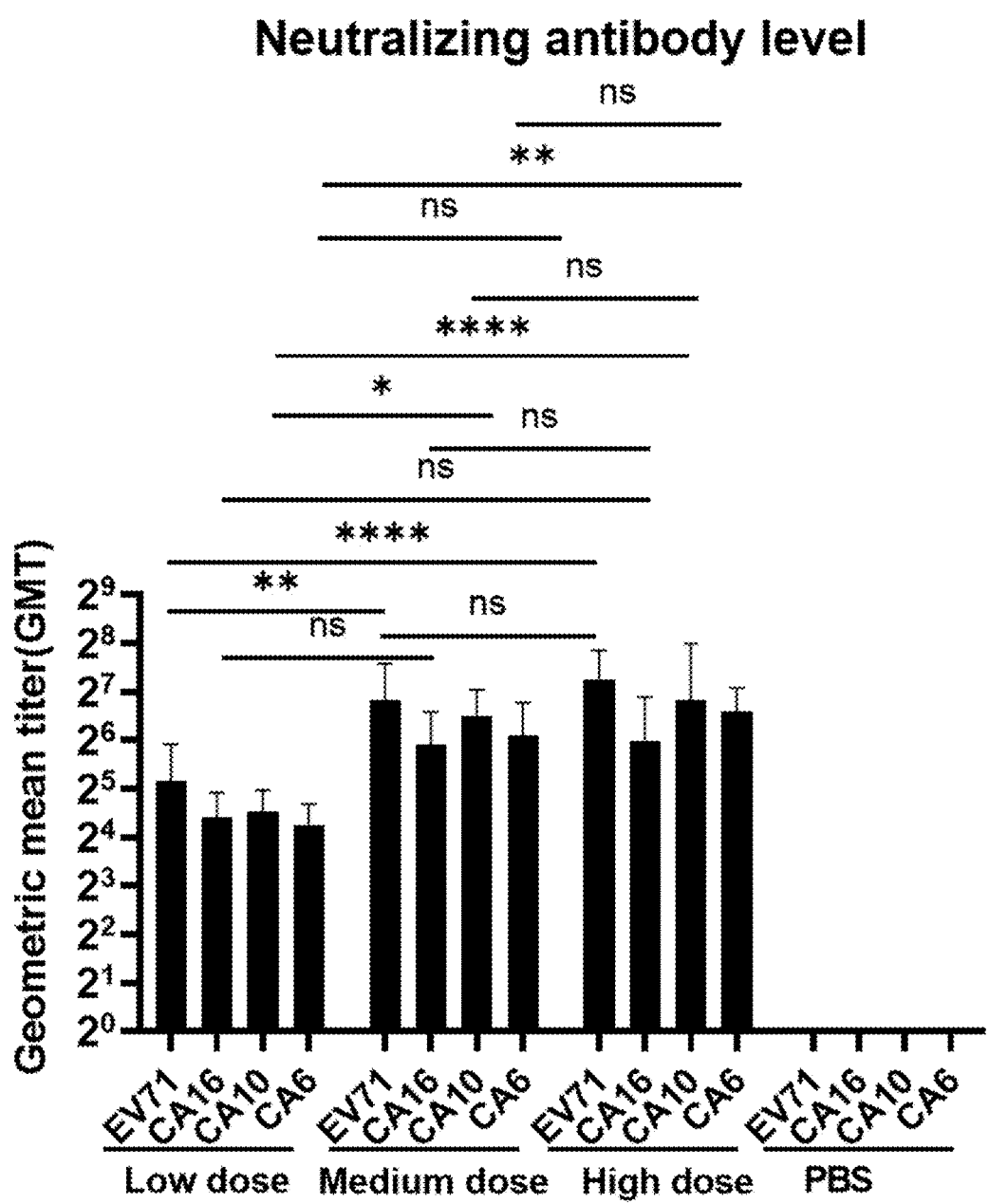
FIG. 3 illustrates an analysis diagram of neutralizing antibody levels against four kinds of enteroviruses after secondary immunization of mice with the multivalent vaccine according to an embodiment 5 of the disclosure.
Figure 4A:
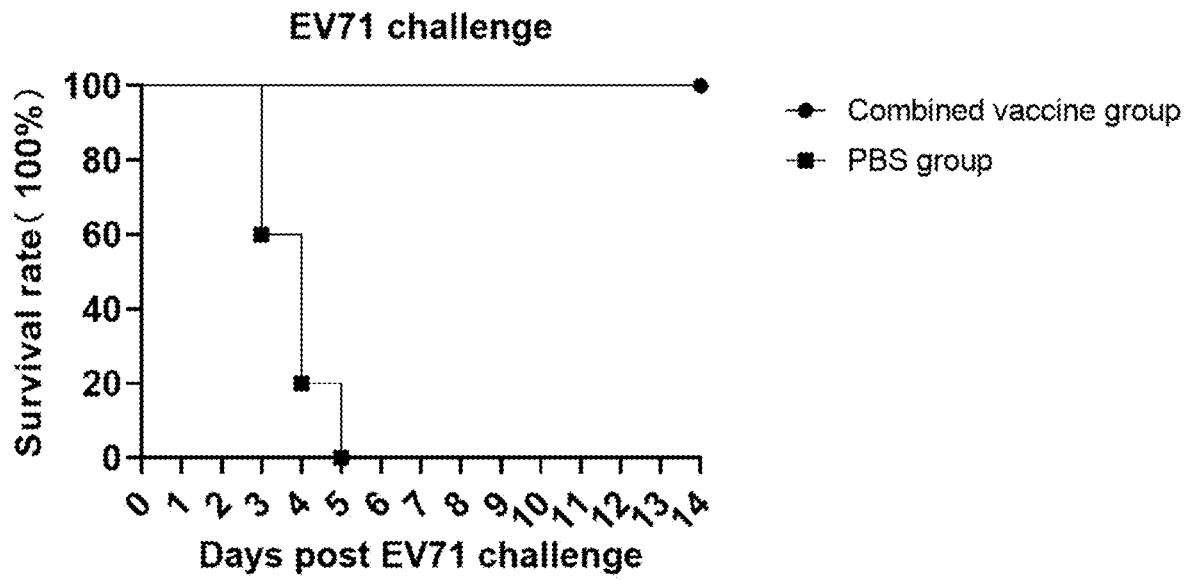
FIGS. 4A-4D illustrate analysis diagrams of protective effects of the multivalent vaccine against four kinds of enteroviruses after secondary immunization of mice with the multivalent vaccine according to an embodiment 6 of the disclosure.
Figure 4B:
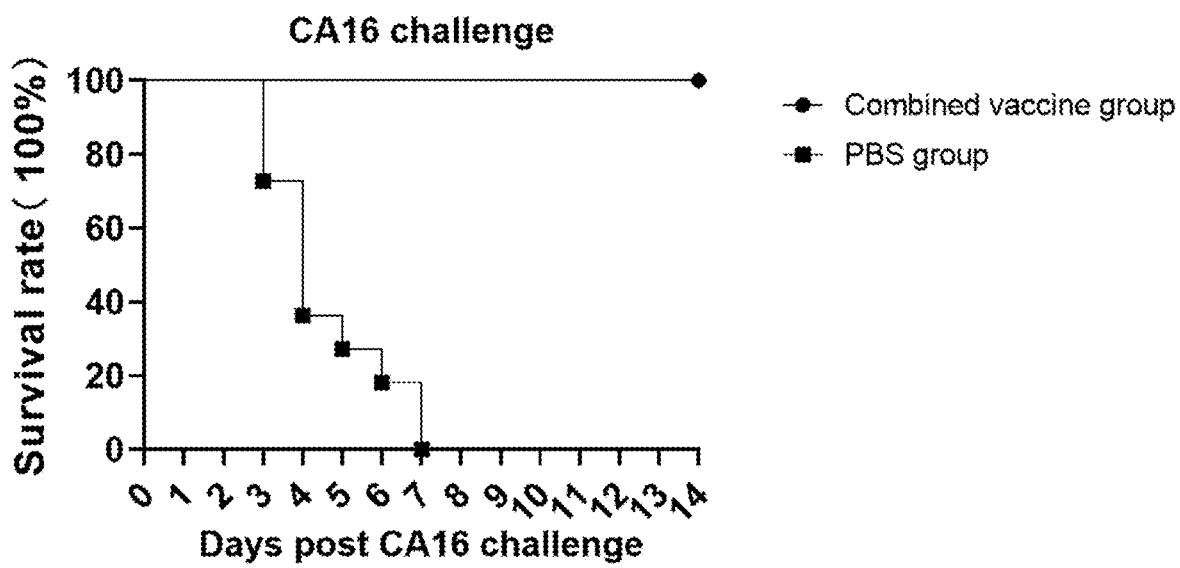
Figure 4C:
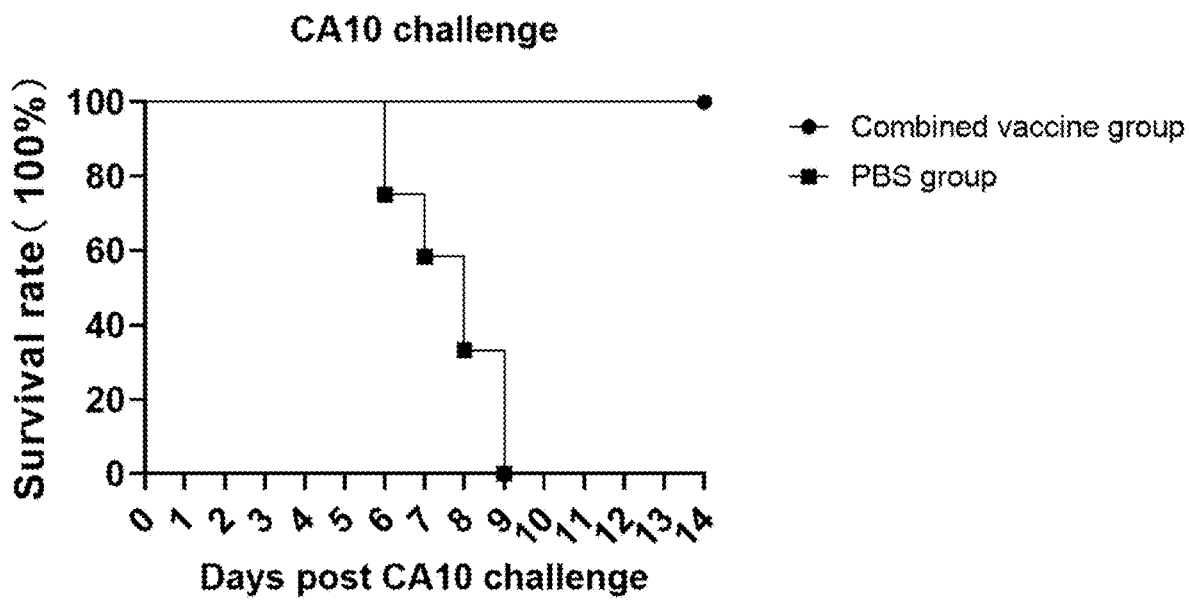
Figure 4D:
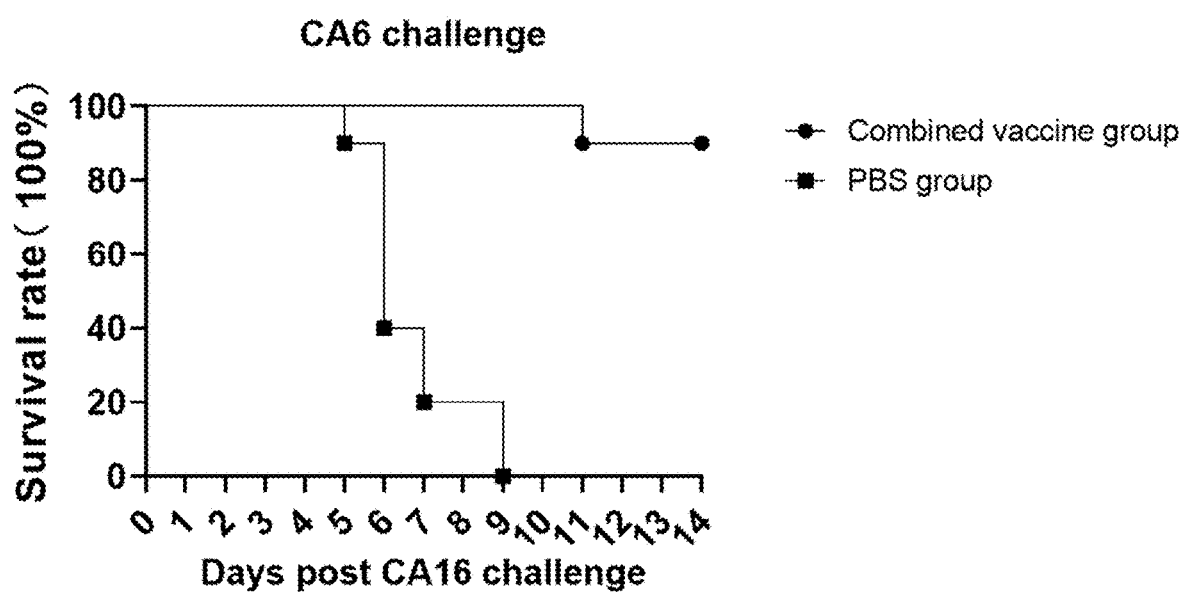

Mice (100 microliters per dose abbreviated as μL/dose) are immunized with three doses of tetravalent combined vaccine in the embodiment 4 according to the procedure of 0 and 21 days, and the titers of serum neutralizing antibodies are detected (Table 1). Vero cells are used for microneutralization experiments and neutralizing antibody titers are detected. Serum is separated 28 days after the completion of the whole immunization, and the diluted serum is neutralized with 100 cell culture infectious dose 50% ($100CCID_{50}$) attack virus for 2 hours and then added to the cells. The cells are cultured at 37° C. for 7 days, and the cytopathic effect is recorded daily. After the completion of two doses of immunization, the antibody positive conversion rate reached 100% (Table 2 and FIG. 3). Specifically, the geometric mean titer (GMT) value of antibody level in the medium dose and high dose groups is significantly higher than that in the low dose group. The antibody level in the medium dose group shows that when the antigen protein content is 10 μg/mouse, good immune effect could be induced.

TABLE 1

Grouping and immunization scheme of C57BL/6 mice

| Experimental group | Number of mice | Injection mode | Immune procedure | Protein dose | Adjuvant |
|---|---|---|---|---|---|
| Low dose | 6 | Intramuscular injection | 0, 21 | 5 μg/mouse | $Al(OH)_3$ |
| Medium dose | 6 | Intramuscular injection | 0, 21 | 10 μg/mouse | $Al(OH)_3$ |
| High dose | 6 | Intramuscular injection | 0, 21 | 20 μg/mouse | $Al(OH)_3$ |

TABLE 2

Positive conversion rate of neutralizing antibody in combined vaccine (100%)

| | Antigen Combined vaccine experimental group | | | |
|---|---|---|---|---|
| Group | EV71[a] | CA16[a] | CA10[a] | CA6[a] |
| Low | 100% | 100% | 100% | 100% |
| Medium | 100% | 100% | 100% | 100% |
| High | 100% | 100% | 100% | 100% |
| PBS | 0% | 0% | 0% | 0% |

In Table 2, [a]: represents the positive conversion rate of neutralizing antibodies against different enteroviruses.

Embodiment 6

Evaluation of Protective Effect of Multi-Epitope Combined Vaccine

The mice are immunized with three groups of tetravalent combined vaccines (enterovirus multi-antigen epitope combined vaccine) in the embodiment 5 according to the procedure of 0 and 21 days. Twenty-eight days after the whole immunization, the female mice immunized with the vaccine are mated with the normal male mice. After the female mice are pregnant and give birth to suckling mice, eight litters of 2-day-old suckling mice are attacked by virus. EV-A71, CV-A16, CV-A10 and CV-A6 viruses are used for virus attack, and each virus attacked 2 litters of suckling mice (the number of suckling mice should be at least 10). The results show that compared with the blank control group, the suckling mice in the experimental group could effectively resist the attacks of four kinds of enteroviruses, among which the protective efficiency of EV71, CA16 and CA10 reached 100% and that of CA6 reached 90% (FIGS. 4A-4D).

Embodiment 7

Safety Evaluation of Multi-Epitope Combined Vaccine

During the evaluation of the tetravalent combined vaccine, all mice are healthy and survived, and their clinical manifestations are normal. The animal safety of the above experimental tetravalent combined vaccine is evaluated, including abnormal toxicity test and acute toxicity test. In the abnormal toxicity test of mice, five specific pathogen-free (SPF) C57BL/6 mice weighing 18-22 g are intraperitoneally injected with 0.5 mL of the tetravalent combined vaccine and observed for 7 days. During the observation period, all mice survived healthily without abnormal reaction, and their weight continued to increase. Therefore, the experimental vaccine meets the requirements. In the acute toxicity experiment of mice, the EV71-CA16-CA6-CA10 combined vaccine is given by the maximum dosage method (80 μg/animal), and no abnormal clinical manifestations and death occurred in the animals.

In summary, the enterovirus multivalent antigen epitope vaccine provided by the disclosure can induce the body to generate specific neutralizing antibodies against EV71, CA16, CA10 and CA6 viruses. In addition to immunogenicity, it is proven to be safe through abnormal toxicity and acute toxicity experiments in mice.

The above is only the illustrated embodiments of the disclosure, and it should be pointed out that those skilled in the art can make several improvements and embellishments without departing from the principle of the disclosure, and these improvements and embellishments should also be regarded as the protection scope of the disclosure.

SEQUENCE LISTING

```
Sequence total quantity: 7
SEQ ID NO: 1           moltype = DNA  length = 1545
FEATURE                Location/Qualifiers
source                 1..1545
                       mol_type = other DNA
                       organism = synthetic construct
SEQUENCE: 1
atgctgagca aggacatcat caagctgctg aacgagcagg tgaacaagga gatgaacagc   60
agcacagtgt acatgagcat gagcagctgg tgctacacac acagcctgga cggcgccggc  120
ctgttcctgt tcgaccacgc cgccgaggag tacgagcacg ccaagaagct gatcatcttc  180
ctgaacgaga caacgtgcc cgtgcagctg accagcatca gcgcccccga gcacaagttc  240
gagggcctga cccagatctt ccagaaggcc tacgagcacg agcagcacat cagcgagagc  300
atcaacaaca tcgtggacca cgccatcaag agcaaggacc acgccacctt caacttcctg  360
cagtggtacg tggccgagca gcacgaggag gaggtgctgt tcaaggacat cctggacaag  420
atcgagctga tcggcaacga gaaccacggc ctgtacctgg ccgaccagta cgtgaagggc  480
atcgccaaga gccgcaagag cagcggtgga ggcgctccca aaccagaatc cagggaatca  540
ggtggaagct ctgggtaccc tacgtttgga gagcataaac aggagaaaga tcttgaatat  600
ggaggtggaa gctctcataa acaggagaaa gatcttgaat atggaggtgg aagctctggg  660
acagtggcag gcggcacagg aacagaagac agtcaccctg gtggaagctc tgatcctgga  720
agggacggcc catggcaatc aacaggtggt agctccggag gaggggctcc aaaacccaca  780
tccagagatt caggtggaag ctctggttat cccacctttg gggagcacct ccaagcaaat  840
gacctagatt atggcggtgg aagctctggc actatcgcag gagggaccgg gaacgaaaac  900
tcccatcctg gtggaagctc tgaccctgga agagatggtc cgtggcagtc cacaggtggt  960
agctccggag gagggctggt aggagttgta gaggtgaagg actcgggcac tagcctagat 1020
ggaggtggaa gctctacata catgcgcttt gatgccgagt tcacttttgt atccaacctc 1080
ggtggaagct ctggggcccc taaaccggat ggtaggaagt caggtggaag ctctggttac 1140
cctacattcg gtgagcacaa acaagccact aatttacaat atgggggtgg aagctctatc 1200
cgaacagtca gtgagtctac tactgggaag aacgtccatg gtggaagctc tacgaagccc 1260
aacggacaag ggttgtaccc tggtggaagc tctgcagtca agaccggtgg agtgtatgat 1320
tactacggtg gtagctccgg aggaggcgcc cccaaaccga cgggaaggga tgccggtgga 1380
agctctggtt accccacttt cggccagcac ccggagacct caaacacaac atacggaggt 1440
ggaagctctg ctggcagagg gtctaacaca aaaccaaatg aagcgcccca cccaggtgga 1500
agctctactg ccaagacagg tgggaattac gattactact aatga              1545

SEQ ID NO: 2           moltype = AA  length = 513
FEATURE                Location/Qualifiers
source                 1..513
                       mol_type = protein
                       organism = synthetic construct
SEQUENCE: 2
MLSKDIIKLL NEQVNKEMNS STVYMSMSSW CYTHSLDGAG LFLFDHAAEE YEHAKKLIIF   60
LNENNVPVQL TSISAPEHKF EGLTQIFQKA YEHEQHISES INNIVDHAIK SKDHATFNFL  120
QWYVAEQHEE EVLFKDILDK IELIGNENHG LYLADQYVKG IAKSRKSSGG GAPKPESRES  180
GGSSGYPTFG EHKQEKDLEY GGGSSHKQEK DLEYGGGSSG TVAGGTGTED SHPGGSSDPG  240
RDGPWQSTGG SSGGGAPKPT SRDSGGSSGY PTFGEHLQAN DLDYGGGSSG TIAGGTGNEN  300
SHPGGSSDPG RDGPWQSTGG SSGGGLVGVV EVKDSGTSLD GGGSSTYMRF DAEFTFVSNL  360
GGSSGAPKPD GRKSGGSSGY PTFGEHKQAT NLQYGGGSSI RTVSESTTGK NVHGGSSTKP  420
NGQGLYPGGS SAVKTGGVYD YYGGSSGGA PKPTGRDAGG SSGYPTFGQH PETSNTTYGG  480
GSSAGRGSNT KPNEAPHPGG SSTAKTGGNY DYY                              513

SEQ ID NO: 3           moltype = DNA  length = 1029
FEATURE                Location/Qualifiers
source                 1..1029
```

```
                        mol_type = other DNA
                        organism = synthetic construct
SEQUENCE: 3
ggcgctccca aaccagaatc cagggaatca ggtggaagct ctgggtaccc tacgtttgga    60
gagcataaac aggagaaaga tcttgaatat ggaggtggaa gctctcataa acaggagaaa   120
gatcttgaat atggaggtgg aagctctggg acagtggcag gcggcacagg aacagaagac   180
agtcaccctg gtgaagctc tgatcctgga agggacggcc catggcaatc aacaggtggt   240
agctccggag gaggggctcc aaaacccaca tccagagatt caggtggaag ctctggttat   300
cccacctttg gggagcacct ccaagcaaat gacctagatt atggcggtgg aagctctggc   360
actatcgcag gagggaccgg gaacgaaaac tcccatcctg gtggaagctc tgaccctgga   420
agagatggtc cgtggcagtc cacaggtggt agctccggag gagggctggt aggagttgta   480
gaggtgaagg actcgggcac tagcctagat ggaggtggaa gctctacata catgcgcttt   540
gatgccgagt tcacttttgt atccaacctc ggtggaagct ctggggcccc taaaccggat   600
ggtaggaagt caggtggaag ctctggttac cctacattcg gtgagcacaa acaagccact   660
aatttacaat atggggtgg aagctctatc cgaacagtca gtgagtctac tactgggaag   720
aacgtccatg gtggaagctc tacgaagccc aacgacaagg gttgtaccc tggtggaagc   780
tctgcagtca agaccggtgg agtgtatgat tactacggt gtagctccgg aggaggcgcc   840
cccaaaccga cggaaggga tgccggtgga agctctggtt acccccacttt cggccagcac   900
ccggagacct caaacacaac atacggaggt ggaagctctg ctggcagagg gtctaacaca   960
aaaccaaatg aagcgcccca cccaggtgga agctctactg ccaagacagg tgggaattac  1020
gattactac                                                          1029

SEQ ID NO: 4            moltype = AA   length = 343
FEATURE                 Location/Qualifiers
source                  1..343
                        mol_type = protein
                        organism = synthetic construct
SEQUENCE: 4
GAPKPESRES GGSSGYPTFG EHKQEKDLEY GGGSSHKQEK DLEYGGGSSG TVAGGTGTED    60
SHPGGSSDPG RDGPWQSTGG SSGGGAPKPT SRDSGGSSGY PTFGEHLQAN DLDYGGGSSG   120
TIAGGTGNEN SHPGGSSDPG RDGPWQSTGG SSGGGLVGVV EVKDSGTSLD GGGSSTYMRF   180
DAEFTFVSNL GGSSGAPKPD GRKSGGSSGY PTFGEHKQAT NLQYGGGSSI RTVSESTTGK   240
NVHGGSSTKP NGQGLYPGGS SAVKTGGVYD YYGGSSGGGA PKPTGRDAGG SSGYPTFGQH   300
PETSNTTYGG GSSAGRGSNT KPNEAPHPGG SSTAKTGGNY DYY                     343

SEQ ID NO: 5            moltype = DNA   length = 1545
FEATURE                 Location/Qualifiers
source                  1..1545
                        mol_type = other DNA
                        organism = synthetic construct
SEQUENCE: 5
atgctgtcca aggacatcat caagctgctg aacgagcagg tgaacaagga gatgaactcc    60
tccaccgtgt acatgtccat gtcctcctgg tgctacactg actcccggga cggagctgga   120
ctgtttctgt ttgatcacgc tgccgaggag tacgagcacg ccaaaaaact gatcatcttc   180
ctgaacgaga caacgtgcc cgtgcagctg acctccattt ccgcccctga catagttc    240
gagggcctga cacagatctt ccagaaggcc tacgagcacg agcagcacat ctccgagtcc   300
atcaacaaca tcgtggacca cgccatcaag tccaaggacc acgccacatt taacttcctg   360
cagtggtacg tggccgagca gcacgaagaa gaggtgctgt ttaaagacat cctggacaag   420
atcgagctga tcggcaacga gaaccacggc ctgtacctgg ccgatcagta tgtgaaggga   480
attgccaaat ccaggaagtc ctccggcggc ggagctccta aacctgaatc cagggaatcc   540
ggcggctcct ccggatatcc tacatttggc gaacacaagc aggaaaagga cctggagtac   600
ggcggcggct ccctcccataa acaagaaaaa gatctggagt acggcggcgg ctcctccgga   660
acagtggctg gaggaacagg aacagaagat tcccatcccg gaggtccctc cgaccctgga   720
agggatggcc cttggcaatc tacaggagga agctccggag gagagctcc taagcctaca   780
tccagggatt ccggaggctc ctccggctat cctacattcg gagagcacct gcaggccaac   840
gacctggatt atgcggagg atcttccgga acaattgccg gcggcacagg aaatgagaac   900
tcccatcccg gcggaagctc cgaccctgga agggatggac cttggcaatc cacaggaggc   960
tcctccggag gagactggt gggagttgtt gaagtgaaag actccggcac atccctggac  1020
ggcggaggat cttccacata tatgaggttc gacgcggagt tcaccttcgt gtccaacctg  1080
ggcgggtcct ccggagctcc aaaacctgat ggaaggaagt ccggaggctc ctccggatat  1140
cctaccttcg gagagcataa acaggccaca aacctgcagt acggcggcgg ctcctccatt  1200
aggacagtgt ccgaatccac aacaggcaag aatgtgcacg gcgggtcctc caccaaaccc  1260
aatggacaag gcctgtaccc cggaggaagc tccgctgtta aacaggcgg agtgtatgac  1320
tattacggcg gctcctccgg cggcggcgcc cccaaaccta caggaagaga tgctggagga  1380
agctccggat atcccacatt tggccaacac cctgaaacct caatacaac ctacggcgga  1440
ggctcctccg ccggcagggg gatctaatact aaacctaacg aagcccctca tcccggaggc  1500
tcctccacag ctaaaaccgg aggaaattat gactactact gatga                  1545

SEQ ID NO: 6            moltype = AA   length = 6
FEATURE                 Location/Qualifiers
source                  1..6
                        mol_type = protein
                        organism = synthetic construct
SEQUENCE: 6
GGSSGG                                                                6
```

-continued

```
SEQ ID NO: 7            moltype = AA  length = 5
FEATURE                 Location/Qualifiers
source                  1..5
                        mol_type = protein
                        organism = synthetic construct
SEQUENCE: 7
EAAAK                                                           5
```

What is claimed is:

1. A recombinant protein, wherein the amino acid sequence of the recombinant protein is shown in SEQ ID NO: 2.

2. A gene encoding the recombinant protein as claimed in claim 1, wherein the nucleotide sequence of the gene is shown in SEQ ID NO: 1.

3. A recombinant vector, comprising:
   the gene as claimed in claim 2, wherein the recombinant vector is pcDNA™3.1$^+$.

4. A cell, comprising:
   the gene as claimed in claim 2, wherein the cell is a 293T cell.

5. A recombinant protein combined vaccine, comprising the recombinant protein as claimed in claim 1 and an adjuvant.

6. The recombinant protein combined vaccine according to claim 5, wherein the adjuvant is one selected from the group consisting of an aluminum hydroxide adjuvant, an aluminum phosphate adjuvant, and an aluminum sulfate adjuvant.

7. A method for preparing the recombinant protein combined vaccine as claimed in claim 5, comprising:
   fusing an enterovirus multi-antigen epitope fusion protein with a Ferritin protein to obtain the recombinant protein; converting the amino acid sequence of the recombinant protein into a nucleotide sequence, constructing pcDNA™3.1$^+$-Ferritin-EV71-CA16-CA6-CA10 expression vector, performing expression, isolation, and purification on the pcDNA™3.1$^+$-Ferritin-EV71-CA16-CA6-CA10 expression vector to obtain a multi-epitope vaccine protein, and adsorbing the multi-epitope vaccine protein using an adjuvant to obtain the recombinant protein combined vaccine.

8. A method for preparing the recombinant protein combined vaccine as claimed in claim 6, comprising:
   fusing an enterovirus multi-antigen epitope fusion protein with a Ferritin protein to obtain the recombinant protein; converting the amino acid sequence of the recombinant protein into a nucleotide sequence, constructing a pcDNA™3.1$^+$-Ferritin-EV71-CA16-CA6-CA10 expression vector, performing expression, isolation, and purification on the pcDNA™3.1$^+$-Ferritin-EV71-CA16-CA6-CA10 expression vector to obtain a multi-epitope vaccine protein, and adsorbing the multi-epitope vaccine protein using the adjuvant to obtain the recombinant protein combined vaccine.

* * * * *